United States Patent
Wang et al.

(10) Patent No.: US 12,235,934 B2
(45) Date of Patent: Feb. 25, 2025

(54) METHOD FOR DISCRIMINATING VERTICAL DISTRIBUTION MODELS OF ORGANIC CARBONS, TERMINAL DEVICE AND NON-TRANSITORY COMPUTER READABLE STORAGE MEDIUM

(71) Applicant: THE SECOND INSTITUTE OF OCEANOGRAPHY (SIO), MNR, Zhejiang (CN)

(72) Inventors: Difeng Wang, Zhejiang (CN); Yan Bai, Zhejiang (CN); Xianqiang He, Zhejiang (CN); Fang Gong, Zhejiang (CN); Teng Li, Zhejiang (CN); Wansong Cui, Zhejiang (CN)

(73) Assignee: THE SECOND INSTITUTE OF OCEANOGRAPHY (SIO), MNR, Zhejiang (CN)

( * ) Notice: Subject to any disclaimer, the term of this patent is extended or adjusted under 35 U.S.C. 154(b) by 310 days.

(21) Appl. No.: 17/590,473

(22) Filed: Feb. 1, 2022

(65) Prior Publication Data
US 2022/0291187 A1    Sep. 15, 2022

(30) Foreign Application Priority Data
Mar. 12, 2021    (CN) ......................... 202110272580.X (51) Int. Cl.
G06F 18/24 (2023.01)
G01C 13/00 (2006.01)
G01N 33/18 (2006.01)
G06F 17/18 (2006.01)
G06F 18/22 (2023.01)

(52) U.S. Cl.
CPC ....... *G06F 18/24765* (2023.01); *G01C 13/00* (2013.01); *G01C 13/008* (2013.01); *G01N 33/1826* (2013.01); *G06F 17/18* (2013.01); *G06F 18/22* (2023.01)

(58) Field of Classification Search
CPC .... G06F 18/24765; G06F 17/18; G06F 18/22; G01C 13/008; G01N 33/1826
See application file for complete search history.

(56) References Cited

PUBLICATIONS

Ogawa et al., "Vertical distributions of dissolved organic carbon and nitrogen in the Southern Ocean" Deep-Sea Research I 46 (1999) 1809-1826 (Year: 1999).*

(Continued)

*Primary Examiner* — John C Kuan
(74) *Attorney, Agent, or Firm* — CANTOR COLBURN LLP (57) ABSTRACT

A method for discriminating vertical distribution models of organic carbons is provided, the method includes: obtaining a concentration of organic carbons in a surface layer of the ocean water area, depths of water of the ocean water area and depths of mixed layers of the ocean water area; determining different vertical distribution models of organic carbons in the ocean water area according to the concentration of the organic carbons in the surface layer and the depths of water of the ocean water area; calculating ratios of the depths of water of the ocean water area to the depths of the mixed layers of the ocean water area; and discriminating the vertical distribution models according to the ratios. According to this method, the accuracy of estimation of the stock of organic carbons in the ocean water area can be improved greatly.

9 Claims, 4 Drawing Sheets

(56) References Cited

PUBLICATIONS

Santinelli et al., "Vertical distribution of dissolved organic carbon (DOC) in the Western Mediterranean Sea in relation to the hydrological characteristics" Deep-Sea Research I 49 (2002) 2203-2219 (Year: 2002).*

Guo et al., "Dynamics of dissolved organic carbon (DOC) in oceanic environments" Oceanography, 40(8), 1995, 1392-1403 (Year: 1996).*

* cited by examiner

METHOD FOR DISCRIMINATING VERTICAL DISTRIBUTION MODELS OF ORGANIC CARBONS, TERMINAL DEVICE AND NON-TRANSITORY COMPUTER READABLE STORAGE MEDIUM

CROSS-REFERENCE TO RELATED APPLICATION

The present application claims priority to Chinese patent application No. 202110272580.X, filed on Mar. 12, 2021 and entitled "method and device for discriminating vertical distribution models of organic carbons, terminal device, and non-transitory computer readable storage medium", the contents of which are incorporated herein by reference in its entirety.

TECHNICAL FIELD

The present application relates to the technical field of ocean ecosystem, and more particularly to a method for discriminating vertical distribution models of organic carbons, a device for discriminating vertical distribution models of organic carbons, a terminal device, and a storage medium.

BACKGROUND

Carbon circle serves as a core of Earth system, has important association with weather, water circulation, nutrient circulation, and productions of biomass of land and ocean, where organic carbons in ocean are taken as the basic parameter of the research on ocean carbon circulation, researches on the types of distribution of organic carbons in ocean and the stock of organic carbons in ocean have played a very important role in the research of ocean carbon circulation.

Currently, the research on the stock of organic carbons in ocean water area is mainly based on a method of combining numerical simulation with measured data, and the measured data is used to estimate the stock of organic carbons by using the integration of the measured data on the depth of water column or by discriminating different water masses. Due to the fact that the distribution of organic carbons in the method for estimating the stock of organic carbons by discriminating different water masses is inhomogeneous, the distribution of the organic carbons cannot be effectively discriminated in the manner of discriminating different water masses, so that an inaccurate estimation of the stock of organic carbons is further resulted. Therefore, a method for discriminating distributions of organic carbons with higher accuracy becomes an important issue that needs to be urgently solved.

SUMMARY

The embodiments of the present application provide a method for discriminating vertical distribution models of organic carbons in ocean water area, a device for discriminating vertical distribution models of organic carbons in ocean water area, a terminal device and a storage medium, which can solve a problem that the accuracy of discrimination of distributions of organic carbons in ocean water area is low in the prior art.

In aspect one, a method for discriminating vertical distribution models of organic carbons in ocean water area is provided in one embodiment of the present application, the method includes steps of:

obtaining a concentration of organic carbons in a surface layer of the ocean water area, depths of water of the ocean water area and depths of mixed layers of the ocean water area;

determining different vertical distribution models of organic carbons in the ocean water area according to the concentration of the organic carbons in the surface layer of the ocean water area and the depths of water of the ocean water area;

calculating ratios of the depths of water of the ocean water area to the depths of the mixed layers of the ocean water area; and discriminating the vertical distribution models of organic carbons in the ocean water area according to the ratios of the depths of water of the ocean water area to the depths of the mixed layers of the ocean water area.

In aspect two, a terminal device is provided in one embodiment of the present application, the terminal device includes a memory, a processor and a computer program stored in the memory and executable by the processor, when the computer program is executed by the processor, the steps in the method for discriminating vertical distribution models of organic carbons in ocean water area in the aspect one are implemented.

In aspect three, a computer readable computer program is provided in one embodiment of the present application, the computer readable storage medium stores a computer program, that, when executed by the processor, causes the processor to implement the steps in the method for discriminating vertical distribution models of organic carbons in ocean water area in the aspect one.

The advantageous effects of the embodiments of the present application over the related art are described as follows: in the embodiments of the present application, firstly, the concentrations of organic carbons in the surface layers of the ocean water area, the depths of water of ocean water area, and the depths of the mixed layers of the ocean water area are obtained, since different ocean water areas with different water depths have different structures and different vertical distributions of organic carbons, so that different vertical distribution models of organic carbons in the ocean water area can be determined according to the concentrations of organic carbons in the surface layers and the depth of water of ocean water area; since the depth of the mixed layer can reflect the mixed state of water, so that the vertical distribution models of organic carbons can be discriminated much better by calculating the relatively mixed state of water, the vertical distribution models of organic carbons are discriminated according to the ratios of depths of water of ocean water area to the depths of the mixed layers of ocean water area, the accuracy of discrimination of vertical distribution models of ocean water area can be improved, and the accuracy of estimation of the stock of organic carbons in the ocean water area is improved accordingly.

BRIEF DESCRIPTION OF THE DRAWINGS

In order to explain the embodiments of the present application more accurately, a brief introduction regarding the accompanying drawings that need to be used in the embodiments is given below; it is apparent that the accompanying drawings described below are only some embodiments of the present application, the person of ordinary skill in the art can also acquire other drawings according to the current drawings without paying creative labor.

EMBODIMENTS OF THE PRESENT APPLICATION

In the following description, in order to describe but not intended to limit the present application, concrete details such as specific system structure, technique, and the like are proposed, so that a comprehensive understanding of the embodiments of the present application is facilitated. However, it will be apparent to the ordinarily skilled one in the art that, the present application can also be implemented in some other embodiments without these concrete details. In some other conditions, detailed explanations of method, circuit, device and system well known to the public are omitted, so that unnecessary details may be prevented from obstructing the description of the present application.

It should be understood that, when a term "comprise/include" is used in the description and annexed claims, the term "comprise/include" indicates existence of the described characteristics, integer, steps, operations, elements and/or components, but not exclude existence or adding of one or more other characteristics, integer, steps, operations, elements, components and/or combination thereof.

It should be further understood that, terms "and/or" used in the description and the annexed claims of the present application are referred to as any combination of one or a plurality of listed item(s) associated with each other and all possible items, and including these combinations.

Additionally, in the descriptions of the specification and the annexed claims, terms such as "first" and "second", "third", etc., are only intended to be discriminated in description, but shouldn't be interpreted as indicating or implying a relative importance.

The descriptions of "referring to one embodiment" and "referring to some embodiments", and the like as described in the specification of the present application means that a specific feature, structure, or characters which are described with reference to this embodiment are included in one embodiment or some embodiments of the present application. Thus, the sentences of "in one embodiment", "in some embodiments", "in some other embodiments", "in other embodiments", and the like in this specification are not necessarily referring to the same embodiment, but instead indicate "one or more embodiments instead of all embodiments", unless there is a special emphasis in other manner otherwise. The terms "comprising", "including", "having" and their variations mean "including but is not limited to", unless there is a special emphasis in other manner otherwise.

It should be understood that, the values of serial numbers of the steps in the aforesaid embodiments do not mean a sequencing of execution sequences of the steps, the execution sequences of the steps should be determined by functionalities and internal logic of the steps, and shouldn't be regarded as limitation to an implementation process of the embodiment of the present application.

Figure 1:
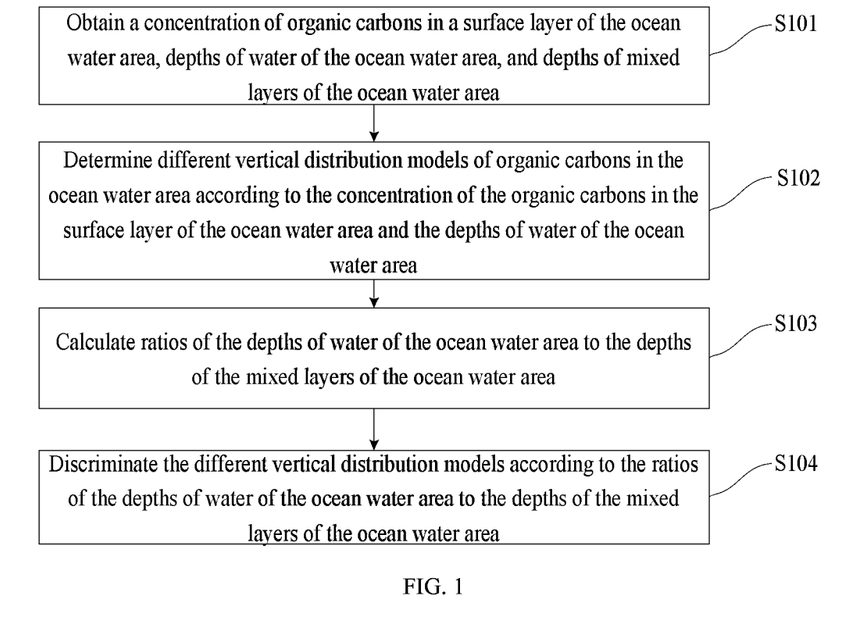
FIG. 1 illustrates a schematic flow diagram of a method for discriminating vertical distribution models of organic carbons in ocean water area according to embodiment one of the present application.

In order to describe the technical solutions of the present application, the technical solutions of the present application will be described with reference to the embodiments below:

Referring to FIG. 1, FIG. 1 illustrates a schematic flowchart of a method for discriminating vertical distribution models of organic carbons in ocean water area according to embodiment one of the present application, as shown in the FIG. 1, the method for discriminating vertical distribution models of organic carbons in ocean water area may include the following steps:

In a step of S101, concentrations of organic carbons of surface layers of ocean water area, water depths of the ocean water area, and water depths of mixed layers of ocean water area are obtained.

In this embodiment of the present application, the organic carbons in the ocean water area are mainly DOC (Dissolved Organic Carbon) and POC (Particulate Organic Carbon), and the concentrations of organic carbons of the surface layers of the ocean water area can be obtained by using an organic carbon concentration remote sensing inversion algorithm. The depths of water of the ocean water area can adopt water depth data in the ETOPO2 data set, where the ETOPO2 is terrain elevation data which includes undersea terrain data, the data source of the undersea terrain data can refer to the following website: https://www.ngdc.noaa.gov/global/etopo2fag.html. Each mixed layer in the ocean water area refers to a uniformly distributed seawater layer caused by disturbances such as wind, heat exchange and water exchange of sea-gas interface, the depth of the mixed layer refers to water depth of water of the seawater layer, and the water depth of the water of the mixed layer can be calculated by the temperature and salinity profile data measured at a station.

In one preferable embodiment, the remote sensing inversion algorithm for the concentration of organic carbons includes:

obtaining a linear relationship between organic carbon and a colored soluble organic substance in a first water area of ocean water area;

obtaining a correspondence relationship between the organic carbon and a temperature of sea surface in a second water area in the ocean water area;

the remote sensing inversion algorithm for the concentration of organic carbons is established according to a multivariate linear regression algorithm, by combining the linear relationship between the organic carbon and the colored soluble organic substance in the first water area of ocean water area with the correspondence relationship between the organic carbon and the temperature of sea surface in the second water area in the ocean water area.

Where, the ocean water area may refer to any water area of the ocean water area, such as a water area in the north of South China Sea. The first water area in the ocean water area may refer to a near-shore area such as a near-shore area in the north of South China Sea, and the second water area in the ocean water area may refer to a sea basin water area such as a sea basin water area in the north of South China Sea. The water of sea basin is classified as one type of ocean water.

It should be understood that, the first water area and the second water area in the ocean water area are classified according to water depths of the ocean water area, for example, the first water area may be a near-shore area which refers to a water area having a water depth less than 150 meters in the ocean water area, and the second water area may be a sea basin water area which refers to a water area having a water depth greater than 1500 meters in the ocean water area, and the ocean water area are classified according to different water depths. The detail of the areas of the first water area and the second water area are not limited in the present application.

In this embodiment of the present application, a remote sensing inversion algorithm for calculating the concentration of DOC is taken as an example, due to the fact that there is a good linear correlation between the concentration of DOC and an absorption coefficient of CDOM in near-shore area, and there is a good relevance between DOC and sea surface temperature, and the water area of the north of South China Sea is affected by near-shore water and has water feature of ocean water area. Thus, in the implementation process of remote sensing inversion algorithm for calculating the concentration of DOC in seawater surface layer in the north of the South China Sea, the remote sensing inversion algorithm for calculating the concentration of DOC in seawater surface layer in the north of the South China Sea is established through the multivariate linear regression method, with the combination of the linear relationship between the DOC concentration in the near-shore region and the CDOM, and the correspondence relationship between the DOC of ocean water and the sea surface temperature.

For example, the remote sensing inversion algorithm for calculating the concentration of DOC in the seawater surface layer in the north of the South China Sea is taken as an example, the linear relationship between the DOC of near-shore area and the CDOM, and the correspondence relationship between the DOC and the sea surface temperature of ocean water are used to establish the remote sensing inversion algorithm for calculating the concentration of DOC in the seawater surface layer in the north of the South China Sea, this algorithm may be formulized as below:

$$\log [a_g(412)] = (-0.8313 \pm 0.0145) - (1.884 \pm 0.037)X + (0.4732 \pm 0.1154)X^2$$

$$DOC = (-22.1 \pm 14.0) + (497 \pm 39)[a_g(412)] + (3.24 \pm 0.55)[SST] - (15.6 \pm 1.6)[a_g(412)][SST]$$

Where, $X = \log[Rrs(488)/Rrs(555)]$, DOC represents the concentration of CDOM of sear water surface in the north of the South China Sea, $a_g$ represents the absorption coefficient of the CDOM, $a_{g(412)}$ represents the absorption coefficient of the CDOM at 412 nm waveband, $R_{rs}$ represents a reflectivity of remote sensing, $R_{rs}(488)$ represents a reflectivity of remote sensing at 488 nm waveband, $R_{rs}(555)$ represents a reflectivity of remote sensing at 555 nm waveband, the reflectivity of remote sensing is calculated according to satellite data which is acquired by a spectrometer, the SST represents the sea surface temperature in the north area of the South China Sea, and the sea surface temperature is obtained through a sea surface temperature detector.

In a step of S102, different vertical distribution models of organic carbons in the ocean water area are determined according to the concentrations of organic carbons in the surface layers of the ocean water area, and the water depths of the ocean water area.

Where the vertical distribution models include but are not limited to a linear attenuation model, an exponential attenuation model, a uniformly mixed distribution model, and a Gaussian distribution model.

In this embodiment of the present application, due to the fact that the terrains, the physiognomies and the seasons of the ocean water area are different, there is a big difference in the distribution of organic carbons in different water areas. Where, due to the fact that the terrains of the ocean water area are different, water depths of the ocean water area are also different, and the obtained water features of the ocean water area are also different since the water depths of the ocean water area are different, the water features are not only related to the depth of water, but also related to seasons, thus, different areas of the ocean water area have different seasonal water features. Since water density can more accurately reflect variations of water masses in some water area under certain circumstances, the aforesaid seasonal water features can be characterized by water densities, and a distribution of organic carbons can be described according to the distribution of water density since there is a higher relevance between water density and the concentration of organic carbons (e.g., a correlation coefficient between water density and the concentration of organic carbons is 0.9).

In this embodiment of the present application, the vertical distribution models of the organic carbons in the ocean water area can be determined by obtaining a vertical distribution structure of a water density in some ocean area in one season, and thereby determining the vertical distribution structure of the organic carbons in this season firstly, and then using a quantitative description method for the vertical distribution structure to determine the vertical distribution model of the organic carbons in this season. The vertical distribution structure of the organic carbons in this season is a mathematical concept, and the vertical distribution model of the organic carbons in this season is obtained by quantitatively describing the vertical distribution structure through a formula.

In one preferable embodiment, the step of determining different vertical distribution models of the organic carbons in the ocean water area according to the concentrations of the organic carbons in the surface layer of the ocean water area and the water depths of the ocean water area includes:
classifying the ocean water area into N water areas according to the water depths of the ocean water area, where N is an integer greater than 1;
determining N seasonal water features of the N water areas according to a target season;
determining different vertical distribution models according to the N seasonal water features and the concentrations of organic carbons in the surface layers of the N water areas.

Where, due to the fact that the terrains of the ocean water area are very complex, the water depths of the various water areas are different, the ocean water area include ocean surface water having a water depth less than 200 meters, ocean medium deep water having a water depth between 200 meters and 700 meters, and ocean deep water having a water depth greater than 900 m, and the ocean water area can also be classified into areas such as a continental slope, a sea basin and the like, since the terrain shapes of the ocean water area are different.

For example, the water areas in the north of the South China Sea is taken as an example, the water areas in the north of the South China Sea can be classified into three water areas of a near-shore with a water depth less than 150 meters, a continental slope with a water depth between 200 meters and 1500 meters and a sea basin with a water depth greater than 1500 meters.

In this embodiment of the present application, there are seasonal changes in the water features of the water areas according to seasons, that is, one water area has different water features in different seasons, so that the seasonal water feature of the water areas need to be determined according to the seasons of the water areas, and different vertical distribution models of the organic carbons are determined according to the seasonal water features and the concentrations of the organic carbons in the surface layers of the ocean water area.

In one preferable embodiment, said determining the seasonal water features of the N water areas according to the target season includes:

obtaining water densities of N water areas according to the target season;

determining the seasonal water features of the N water areas according to the water densities of the N water areas.

In this embodiment of the present application, the water densities of the water areas may be obtained according to sea surface temperatures, sea surface salinity and the intensities of pressures, the sea surface temperatures are different in different seasons and the differences of the sea surface temperatures may also affect the distributions of the sea surface salinity, thus, water densities detected in the same water area are also different in different seasons, and the difference of water densities determines that the seasonal water features of the water areas are also different. The target season may refer to a season of a water area when the water density of the water area is detected.

In particular, a water density of some water area may be obtained through a water density profile distribution diagram of this water area, and a seasonal water feature of this water area may be determined by analyzing according to the calculated water density of the water area in the target season.

As an example, the three water areas classified from the north of the South China Sea are taken as an example, assuming that the target season is summer, a profile distribution diagram of water density in summer is obtained, by analyzing the profile distribution diagram, it is concluded that the water densities of the near-shore water areas are increased in a step-like manner, thus, it can be determined that the seasonal water feature of the near-shore water areas has a density distribution structure that reflects increasing of densities in a step-like manner when the target season is summer; it can also be concluded that the water densities in the continental slope water area and the sea basin water area are increased exponentially, thus, it can be determined that the seasonal water features in the continental slope water area and the sea basin water area have an exponentially increased density distribution structure when the target season is summer.

As an example, if the target season is winter, a profile of water densities of one water area in the winter is obtained, by analyzing the profile distribution diagram of water densities, it is concluded that the water densities of the near-shore water area has a uniformly mixed distribution structure up and down, and it can be determined that the seasonal water features of the near-shore water areas have uniformly mixed density distribution structure up and down when the target season is winter; it can also be concluded that there exists obvious mixed layer in the upper layer of seawater in the continental slope and sea basin water areas, the density of the mixed layer does not change with the change of water depth, and the water density below the mixed layer is increased rapidly with the increase of water depth, thus, it can be determined that the seasonal water features of the continental slope water area and the sea basin water areas have a mixed structure composed of a deeper mixed layer and an exponentially increasing water density distribution in the upper layer, when the target season is winter.

It should be understood that the profile distribution diagram of water densities is obtained by calculating the water densities of the water areas, and the water densities are calculated according to the temperatures, the salinity and the intensities of pressures of the sea surface. The temperatures, the salinity and the intensities of pressures of the sea surface can be measured by a CTD (Conductivity Temperature Depth) measurement system.

In one preferable embodiment, the step of determining different vertical distribution models according to the seasonal water features and the concentration of organic carbons of the surface layers of the N water areas includes:

determining different vertical distribution structures of the organic carbons in the N water areas in the target season according to the seasonal water features of the N water areas;

determining the different vertical distribution models according to different vertical distribution structures and the concentration of organic carbons of the surface layers.

In this embodiment of the present application, there is a correlation between the vertical distribution structures of the organic carbons in the ocean water area and the water densities, in the water areas of the north of the South China Sea, the seasonal water features of the water areas are characterized by water densities (available from the above analysis), thus, different vertical distribution structures of the organic carbons in the N water areas in different target seasons can be determined by analyzing seasonal water features of the N water areas. Since the vertical distribution model of the organic carbons in the target season is obtained by quantitatively describing the vertical distribution structure of the target season according to a formula, the concentration of organic carbons of the surface layer which is obtained through the remote sensing inversion algorithm for calculating concentration of organic carbons needs to be used as an important parameter of the formula.

Figure 3:
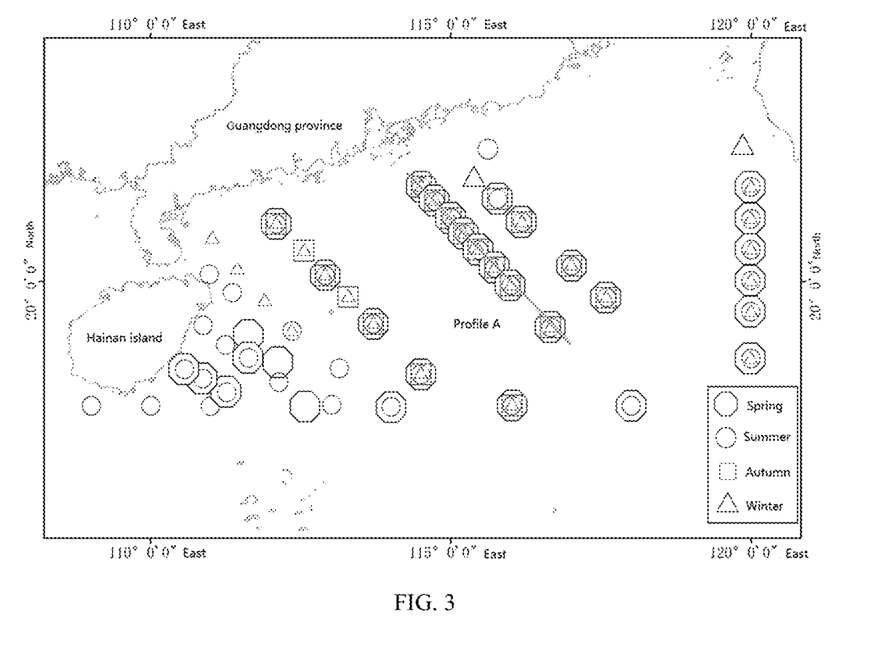
FIG. 3 illustrates a schematic diagram of a profile A.

As an example, the distribution of the profile of DOC is analyzed using a typical profile A of the ocean water area, where FIG. 3 is a schematic diagram of the position of the profile A, and the icons represent sampling points in the north of the South China Sea in different seasons, the octagon icon, the circle icon, the square icon and the triangular icon represent the sampling points in the north of the South China Sea in Spring, Summer, Autumn and Winter respectively, where the section A includes common sampling points in the north of South China Sea in Spring, Summer, Autumn and Winter. Taking the target season as spring as an example, in the near-shore sea area of the north of the South China Sea, the water density is increased in a step-like manner with the increase of water depth, and the distribution of profile of DOC has a step-like linear attenuation structure, the water density has such a structure that the upper layer is a shallow mixing layer and the lower layer is exponentially increased in the continental slope water area and the sea basin water area in the north of the South China Sea, moreover, there is a shallow mixing layer in the distribution of profile of DOC, then, the water density is exponentially attenuated; thus, it can be determined that the vertical distribution structure of DOC of the near-shore water area in the north of the South China Sea in spring has a linear attenuation distribution, and the vertical distribution structure of DOC in the continental slope water area and the sea basin water area has an exponential attenuation distribution.

As an example, taking the target season as winter as an example, in the near-shore area in the north of the South China Sea, the densities of water are uniformly distributed up and down, the profile of DOC is uniformly distributed up and down, and the vertical distributions of water densities and DOC in the continental slope water area and the sea basin water area in the north of the South China Sea appear that there is an obvious mixing layer in the upper layer, and water density is exponentially increased in the lower layer; therefore, it can be determined that the vertical distribution structure of DOC in the north of South China Sea in winter has a uniformly mixed distribution type and an exponential attenuation distribution type.

Figure 4:
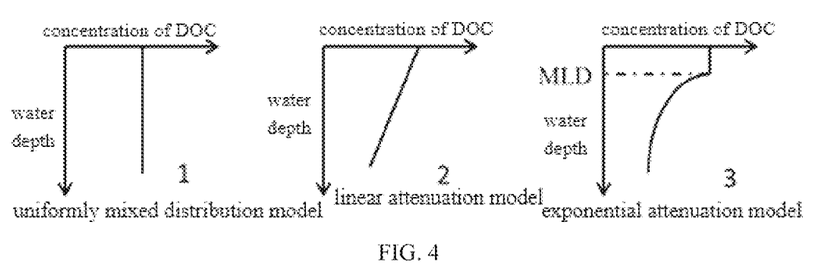
FIG. 4 illustrates a diagram of an example of a vertical distribution model of organic carbons in ocean water area.

In particular, the different vertical distribution models of DOC in the north of the South China Sea is obtained through quantitative description according to the different vertical distribution structures of DOC. There are linear attenuation distribution and exponential attenuation distribution in spring and there are uniformly mixed distribution and exponential attenuation distribution in winter, as shown in FIG. 4, 1 represents a uniformly mixed distribution, 2 represents a linear attenuation distribution, 3 represents an exponential attenuation distribution, the vertical distribution models of DOC of water areas in the north of South China Sea can be represented by the aforesaid three distributions, and the distribution model may be expressed by the formulas listed below:

$$DOC_z = DOC_0 \ (0 \le z \le \text{Depth}) \text{ (uniformly mixed model)}$$

$$DOC_z = DOC_0 + k_1 \cdot z \ (0 \le z \le \text{Depth}) \text{ (linear attenuation model)}$$

$$\begin{cases} DOC_z = DOC_0 (z \le z_m) \\ DOC_z = y_0 + DOC_0 \cdot e^{\left(-\frac{z-z_0)^2}{t_1}\right)} (\text{Depth} \ge z > z_m) \end{cases}$$

(exponential attenuation model)

Where, $DOC_z$ represents the concentration of DOC in the ocean water area having a water depth z, $DOC_0$ represents the concentration of DOC in the surface layer of the ocean water area, Depth represents the depths of water of the ocean water area, $k_1$ represents a slope of a linear attenuation model, $y_0$, $x_0$, and $t_1$ are all constant parameters of the exponential attenuation model obtained by fitting, and $Z_m$ represents the depth of the mixed layer.

It should be understood that, regarding some water area in the ocean water area, Depth represents the depth of water in this water area, and Z represents one of water depths of this water area.

In a step of S103, ratios of depths of water of the ocean water area to depths of mixed layers of the ocean water area are calculated.

In this embodiment of the present application, each mixed layer refers to a uniformly distributed seawater layer caused by disturbances such as wind, heat exchange, and water exchange of the sea-gas interface. When the temperature and the salinity of seawater in the upper layer are in a relatively uniformly mixed state, the depth of the mixed layer can reflect the mixed state of the water areas. When the water area is completely and uniformly mixed, the depth of the mixed layer can be considered as being equal to the depth of water; when the stratification phenomenon is significant, a ratio of the depth of the mixed layer to the depth of water is relatively small. Therefore, the calculated ratios of the depths of the mixed layer to the depths of water of ocean water area can reflect a mixed state of the water areas to some extent, the vertical distribution models of organic carbons in different water areas can be discriminated according to the mixed state of the water areas.

In particular, the calculation of the ratios of depths of water of the ocean water area to the depths of the mixed layers of the ocean water area may be expressed by the formula listed below:

$$\alpha = \text{Depth/MLD}$$

Where $\alpha$ represents a ratio of water depth to the depths of the mixed layers of the ocean water area, Depth represents water depth of the ocean water area, MLD represents the depth of the mixed layer. ETOPO2 data set is used for depth data, and MLD can be obtained by calculation according to profile CTD data from the measured station.

In a step of S104, different vertical distribution models are discriminated according to the ratios of depths of water to the depths of the mixed layers of the ocean water area.

In this embodiment of the present application, the ratios of the depths of water of the ocean water area to the depths of the mixed layers of the ocean water area may reflect mixed state of water (i.e., the vertical distribution structures of water densities), then, the vertical distribution models of DOC can be obtained according to the vertical distribution structures of water densities according to the aforesaid steps, said discriminating the different vertical distribution models according to the ratios of depths of water of the ocean water area to the depths of the mixed layers of the ocean water area can refer to discriminating the water areas according to the different vertical distribution models, thereby obtains the vertical distribution models of these water areas.

In one preferable embodiment, discriminating different vertical distribution models according to the ratios of the depths of water of the ocean water area to the depths of the mixed layers of the ocean water area includes:

determining discrimination threshold values of different vertical distribution models according to the ratios of the depths of water of the ocean water area to the depths of the mixed layers of the ocean water area;

discriminating the vertical distribution models according to the ratios of the depths of water of the ocean water area to the depths of the mixed layers of the ocean water area, and the discrimination threshold values.

In this embodiment of the present application, since the ratios of the depths of water of the ocean water area to the depths of the mixed layers of the ocean water area are related to the target season, and the discrimination threshold values of the vertical distribution models are determined according to the calculated ratios, thus, the obtained discrimination threshold values of the vertical distribution models are also different when target seasons are different.

In particular, in order to discriminate different vertical distribution models according to the ratios and the discrimination threshold values of the vertical distribution models, it needs to determine a target season first, and the ratios of the depths of water of the ocean water area to the depths of the mixed layers of the ocean water area in the target season are calculated, then, the discrimination threshold values are set according to the ratios of the depths of water of the ocean water area to the depths of the mixed layers of the ocean water area in the target season, finally, different vertical distribution models of the ocean water area in the target season are discriminated according to the discrimination threshold values.

As an example, the target season is determined as spring, and the calculated ratio $\alpha$ of the depths of water to the depths of the mixed layers in the near-shore water area in the north of South China Sea is greater than 5, and there is obvious stratification phenomenon in the sea basin water areas and the continental slope water areas, the ratios of the depths of water to the depths of the mixed layers in the sea basin water area and the continental slope water area are greater than the ratios of the depths of water to the depths of the mixed layers in the near-shore water area, the discrimination threshold value may be set as 10 according to the obtained value of $\alpha$, and the discrimination threshold value can be used to discriminate the linear attenuation model from the exponential attenuation model better.

As an example, the target season is determined as winter, the calculated ratio $\alpha$ of the near-shore water area in the north of the South China Sea is less than 2, and the ratio $\alpha$ of the depths of water to the depths of the mixed layers in the sea basin water area and the continental slope water area are greater than 2, and the discrimination threshold value can be set as 2, the discrimination threshold value can discriminate the uniformly mixed distribution model from the exponential attenuation model better.

In one preferable embodiment, the step of discriminating different vertical distribution models according to the ratios of the depths of water to the depths of the mixed layers in ocean water area and the discrimination threshold values includes:

comparing the ratios of the depths of water to the depths of the mixed layers in ocean water area with the discrimination threshold values to obtain comparison results;

discriminating different vertical distribution models according to the comparison results.

Where, due to the fact that the vertical distribution models of organic carbons in different water areas of the ocean water area are different, discriminating different vertical distribution models is equal to discriminating the vertical distribution models of organic carbons in different water areas of the ocean water area.

In this embodiment of the present application, the calculated ratios of the depths of water of the ocean water area to the depths of the mixed layers of the ocean water area are compared with the discrimination threshold values of the target season to obtain the comparison results (the ratios are greater than the discrimination threshold values or the ratios are less than the discrimination threshold values), and the t vertical distribution models are discriminated according to the comparison results, where the different vertical distribution models refer to different vertical distribution models of organic carbons.

As an example, if the target season is spring, and the discrimination threshold value is set as 10, when it is determined that the ratio of the depth of water to the depth of the mixed layer in one water area of the ocean water area are 12 (i.e., the ratio is greater than or equal to the discrimination threshold value), the vertical distribution model of DOC in the water area is determined as the exponential attenuation model; when it is determined that the ratio of the depth of water to the depth of the mixed layer in one water area of the ocean water area is 8 (i.e., the ratio is less than the discrimination threshold value), the vertical distribution model of DOC in the water areas is determined as the linear attenuation model.

As an example, if the target season is winter, and the discrimination threshold values is set as 2, when it is determined that the ratio of the depth of water to the depth of the mixed layer in one water area of the ocean water area is 4 (i.e., the ratio is greater than or equal to the discrimination threshold value), the vertical distribution model of the water area is determined as the exponential attenuation model; when it is determined that the ratio of the depth of water to the depth of the mixed layer in one water area of the ocean water area is 0.5 (i.e., the ratio less than the discrimination threshold value), the vertical distribution model of the water area is determined as the uniformly mixed distribution model.

It should be understood that the organic carbons involved in the steps mentioned above may be DOC (Dissolved Organic Carbons) or POC (Particle Organic Carbons), different organic carbons may have different vertical distribution models, the organic carbons can be analyzed to finally discriminate the vertical distribution models of the organic carbons in each of the water areas according to the aforesaid steps.

In the embodiments of the present application, the concentrations of organic carbons in the surface layers of the ocean water, the depths of water of the ocean water area and the depths of the mixed layers of the ocean water area are obtained, due to the fact that the ocean water area of different water depths have different structures, and the vertical distribution models of the organic carbons are also different, so that different vertical distribution models of the organic carbons in the ocean water area are determined according to the concentration of organic carbons of the surface layer and the depths of water of the ocean water area; since the depths of the mixed layers can reflect the mixed state of water, the vertical distribution models of the organic carbons can be better discriminated by calculating the relatively mixed state of water, thus, the vertical distribution models of organic carbons are discriminated according to the ratios of the depths of water of the ocean water area to the depths of the mixed layers, and the accuracy of discrimination of the vertical distribution models of organic carbons can be improved.

Figure 2:
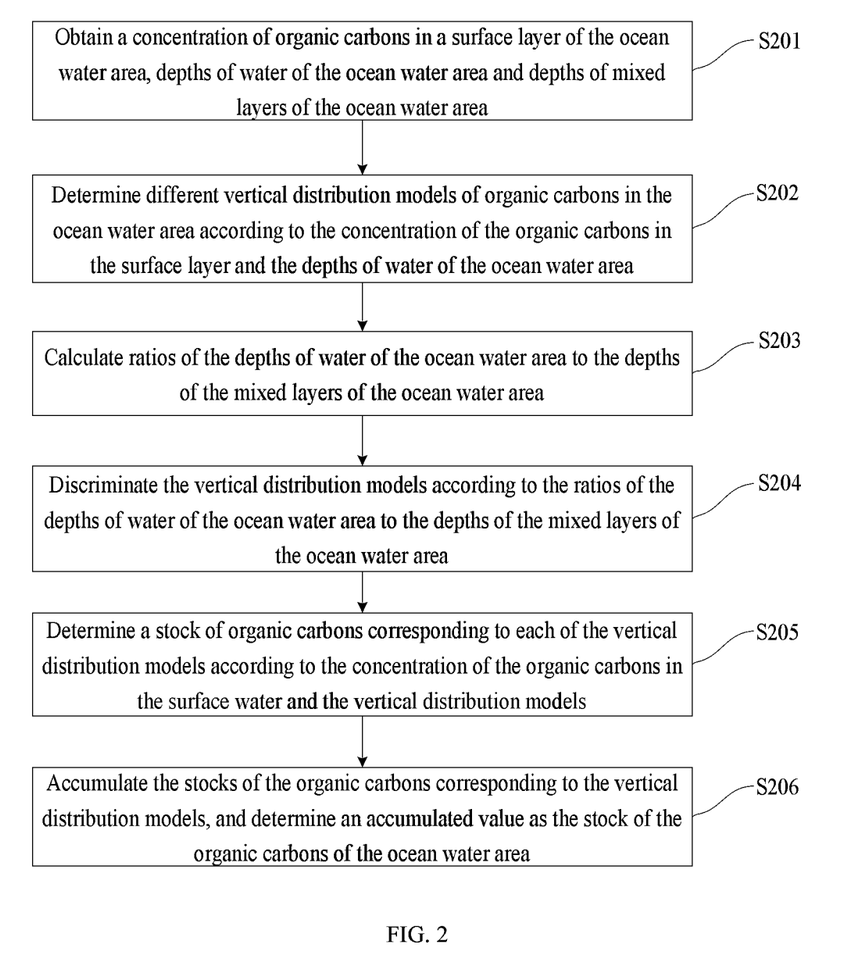
FIG. 2 illustrates a schematic flow diagram of a method for discriminating vertical distribution models of organic carbons in ocean water area according to embodiment two of the present application.

Referring to FIG. 2, FIG. 2 illustrates a schematic flowchart of a method for discriminating vertical distribution models of organic carbon in ocean water area according to embodiment two of the present application, as shown in FIG. 2, the method for discriminating vertical distribution models of organic carbons in the ocean water area may include the following steps:

In a step of S201, the concentrations of organic carbons in the surface layers of the ocean water area, the water depths of the ocean water area, and the depths of the mixed layers of the ocean water area are obtained.

In this embodiment of this application, the step of obtaining the concentrations of organic carbons in the surface layers of the ocean water area is similar to the step S101, it should be noted that the concentrations of organic carbons in the surface layers is obtained by using a remote sensing inversion algorithm, however, methods for obtaining the concentrations of different organic carbons in the surface layers are also different. For example, the remote sensing inversion algorithm for calculating the concentration of DOC is established by combining the linear relationship between DOC and CDOM in the near-shore area with the correspondence relationship between the DOC of the ocean water and sea surface temperature; and the remote sensing inversion algorithm for calculating the concentration of POC is established according to the linear relationship between the POC and the particle attenuation coefficient, so that the concentration of POC in the surface layer is obtained.

It should be understood that, the step of obtaining depths of water of the ocean water area and the depths of the mixed layers of the ocean water area are similar to the step S101 in the embodiment mentioned above, reference can be made to each other, this step will not be repeatedly described herein.

In a step of S202, different vertical distribution models of organic carbons in the ocean water area are determined according to the concentrations of organic carbons in the surface layers of the ocean water area and depths of water of the ocean water area.

In this embodiment of the present application, regarding the POC (Particle Organic Carbon), the analysis method for determining the vertical distribution models of the POC in the ocean water area is similar to the step S102 in the embodiment described above, reference can be made to each other. According to this analysis method, it is determined that the vertical distribution models of the POC in the ocean water area are the uniformly mixed distribution model, the exponential attenuation model and the Gaussian distribution model, and these models may be expressed by the formulas listed below:

$$POC_z = POC_0$$

($0 \leq z \leq$ Depth) (uniformly mixed distribution model)

$$POC_Z = POC_0 \left( y_1 + ae^{\frac{-z(z-z_1)^2}{\sigma^2}} \Big/ \sigma\sqrt{\pi/2} \right)$$

($0 \leq z \leq$ Depth) (Gaussian distribution model)

$$POC_Z = POC_0 + POC_0 \left( y_2 + A_1 \cdot e^{-k_2(z-z_2)} \right)$$

($0 \leq z \leq$ Depth) (exponential attenuation model)

where $y_1$, $a$, $z_1$, and $\sigma$ are constant parameters of the Gaussian distribution model obtained by fitting, $y_2$, $A_1$, $K_2$ and $Z_2$ are all constant parameters of the exponential attenuation model obtained by fitting; Depth represents the depths of water of the ocean water area; $POC_0$ represents the concentration of POC in the surface layer; $POC_z$ represents the concentration of POC of ocean water with a water depth z.

In a step of S203, ratios of depths of water of the ocean water area to the depths of the mixed layers of the ocean water area are calculated.

The step S203 in this embodiment is similar to the step S103 in the aforesaid embodiment, reference can be made to each other, the details of this embodiment are not repeatedly described herein.

In a step of S204, different vertical distribution models are discriminated according to the ratios of depths of water of the ocean water area to the depths of the mixed layers of the ocean water area.

In this embodiment of the present application, considering that there are different vertical distribution models for POC and there are different target seasons, the discriminating threshold value in spring may be set as 7.5, and the discrimination threshold value in winter may be set as 2.

In implementation, if the target season is spring, and a ratio of depth of water to depth of mixed layer in one water area of the ocean water area is determined as 9 (i.e., the ratio is greater than or equal to the discrimination value), the vertical distribution model of POC in this water area is the Gaussian distribution model; if a ratio of depth of water to depth of mixed layer in one water area of the ocean water area is determined as 6 (i.e., the ratio is lower than the discrimination value), it is concluded that the vertical distribution model of POC in this water area is the uniformly mixed distribution model.

If the target season is winter, and a ratio of depth of water to depth of mixed layer in one water area of the ocean water area is determined as 5 (i.e., the ratio is greater than or equal to the discrimination value), the vertical distribution model of POC in this water area is determined as the exponential attenuation model; if a ratio of depth of water to depth of mixed layer in one water area of the ocean water area is determined as 1 (i.e., the ratio is lower than the discrimination value), it is concluded that the vertical distribution model of POC in this water area is the uniformly mixed distribution model.

In a step of S205, a stock of organic carbons corresponding to one vertical distribution model is determined according to the concentrations of organic carbons in the surface layers and the vertical distribution model.

In this embodiment of the present application, the stock of organic carbons corresponding to each vertical distribution model may be determined by integrating the concentrations of organic carbons in the surface layers and this vertical distribution model, in particular, the integral formula for the stock of organic carbons may be expressed by the formula listed below:

$$OC_{stock} = \int_0^h OC_0 \times f(z) dz$$

Where, $OC_{stock}$ represents the stock of organic carbons, $OC_0$ represents the concentration of the organic carbons in the surface layer of the ocean water area, Z represents a depth of a water area corresponding to a determined vertical distribution model of organic carbons, and H represents the integration of depths of the stock of organic carbons; $OC_{stock}$ represents the stock of DOC corresponding to the determined vertical distribution model of DOC when the organic carbon is DOC, $OC_0$ represents the concentration of DOC in the surface layer of the ocean water area, f(z) represents the determined vertical distribution model of DOC, Z represents a water depth of one water area corresponding to the determined vertical model of DOC; when the organic carbon is POC, $OC_{stock}$ represents the stock of organic carbons corresponding to the determined vertical distribution model of POC, $OC_0$ represents the concentration of POC in the surface layer of the ocean water area, f(z) represents the determined vertical distribution model of DOC, Z represents a water depth of one water area corresponding to the determined vertical model of POC.

In a step of S206, the stocks of organic carbons corresponding to different vertical distribution models are accumulated, and the obtained accumulated value is determined as the stock of organic carbons in the ocean water area.

In this embodiment of the present application, the stock of organic carbons of the ocean water area may be determined by accumulating the stocks of organic carbons corresponding to different vertical distribution models, where the stock of the organic carbons of the ocean water area refers to the stock of organic carbons per season.

In particular, the stock of DOC in an euphotic layer of ocean water area in spring is calculated, it can be known from the step S104 that the vertical distribution models of the north of South China Sea includes an exponential attenuation distribution model and a linear attenuation distribution model; firstly, the water depths of the water area corresponding to the determined exponential attenuation distribution model are obtained, the water depths of the water area in the euphotic layer are obtained as the integral depth of the stock of organic carbons, the concentration of DOC in the surface layer, the exponential attenuation model, the water depths of the water area corresponding to the determined exponential attenuation distribution model, and the depths of water in the euphotic layer are substituted into the formula to integrate the stock of organic carbons, so that the stock of DOC in the euphotic layer of the ocean water area in spring can be obtained, where the DOC belongs to the exponential attenuation distribution model; secondly, the water depths of water area in the euphotic layer are obtained according to water depths of water area corresponding to the determined linear attenuation distribution model, and are taken as the integration of depths, the concentration of DOC in the surface layer, the linear attenuation distribution model, the water depths of the water area corresponding to the determined linear attenuation distribution model, and the depths of water in the euphotic layer are substituted into the formula to integrate the stock of organic carbons, so that the stock of DOC in the euphotic layer of the ocean water area in spring can be obtained, where the DOC belongs to the linear attenuation distribution model; finally, the stock of DOC that conforms to the exponential attenuation distribution model and the stock of DOC that conforms to the linear attenuation distribution model are accumulated to obtain the stock of DOC in the euphotic layer of the ocean water area in spring.

It should be noted that, when calculating the stock of organic carbons in the euphotic layer, the depth of water in the euphotic layer may be obtained as the integral depth of the stock of organic carbons, if the stock of organic carbons in other water layer in the ocean water area needs to be calculated, the depths of water in the other water layer needs to be obtained as the integral depth of the stock of organic carbons, that is, the water depths of one water layer corresponding to the stock of organic carbons is obtained as the integral depth of the stock of organic carbons, the integral depth of the stock of organic carbons in the formula for integrating the stock of organic carbons may be any depth, which is not limited herein.

It should be understood that, the method for obtaining the stock of POC in the euphotic layer of the ocean water area in four seasons of spring, summer, autumn and winter, and the method for obtaining the stock of DOC in the three seasons of summer, autumn and winter are as same as the methods in the steps mentioned above, so that the details of the methods are not repeatedly described herein.

In the present application, the vertical distribution models of organic carbons are discriminated, and the stocks of organic carbons in the water areas are calculated according to the water areas corresponding to the vertical distribution models of organic carbons, finally, the stocks of organic carbons in the water areas are accumulated to obtain the stock of organic carbons in the ocean water area, according to the technical solution mentioned above, the accuracy of discrimination of the vertical distribution models of organic carbons can be improved, and the accuracy of estimation of the stock of organic carbons in the ocean is further improved.

Figure 5:
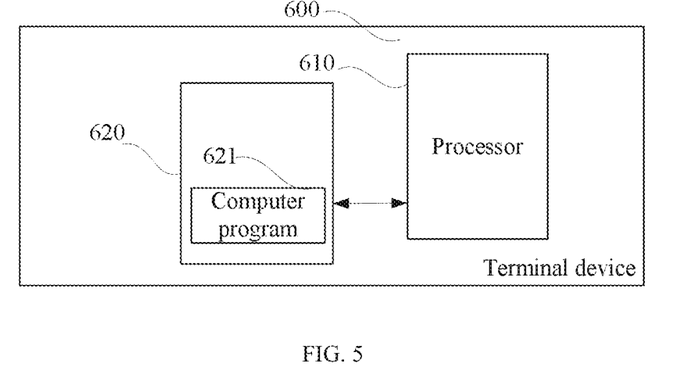
FIG. 5 illustrates a schematic diagram of a structure of a terminal device according to embodiment four of the present application.

FIG. 5 illustrates a schematic diagram of a structure of a terminal device provided by embodiment four of the present application. As shown in FIG. 5, the terminal device 600 in this embodiment includes: at least one processor 610 (only one processor is shown in FIG. 5), a memory 620 and a computer program 621 stored in the memory 620 and executable by the at least one processor 610, when the processor 610 executes the computer program 621, the steps in the method embodiment of discriminating vertical distribution models of organic carbons in the ocean water areas are implemented.

The terminal device 600 can be a computing device such as a desktop computer, a laptop computer, a palm computer, a cloud server, etc. The terminal device 600 can include but is not limited to: a processor 610, a memory 620. The person of ordinary skill in the art can understand that, FIG. 5 only illustrates an example of the terminal device 600, but should not be constituted as limitation to the terminal device 600, more or less components than the components shown in FIG. 5 may be included, or some components or different components may be combined; for example, the terminal device 600 can also include an input and output device, a network access device, etc.

The so-called processor 610 may be CPU (Central Processing Unit), and can also be other general purpose processor, DSP (Digital Signal Processor), ASIC (Application Specific Integrated Circuit), FGPA (Field-Programmable Gate Array), or some other programmable logic devices, discrete gate or transistor logic device, discrete hardware component, etc. The general purpose processor may be a microprocessor, as an alternative, the processor can also be any conventional processor, and the like.

The memory 620 may be an internal storage unit of the terminal device 600, such as a hard disk or a memory of the terminal device 600. The memory 620 may also be an external storage device of the terminal device 600, such as a plug-in hard disk, a SMC (Smart Media Card), a SD (Secure Digital) card, a FC (Flash Card) equipped on the terminal device 600. Furthermore, the memory 620 may not only include the internal storage unit of the terminal device 600 but also include the external memory. The memory 620 is configured to store the operating system, applications, BootLoader, data and other procedures such as program codes of the computer program, etc. The memory 620 can also be configured to store data that has been output or being ready to be output temporarily.

In the aforesaid embodiments, the descriptions of the embodiments are emphasized respectively, regarding the part of an embodiment which isn't described or disclosed in detail, reference can be made to relevant descriptions in some other embodiments.

The person of ordinary skill in the art may be aware of the fact that, the elements and algorithm steps of the various examples described in combination with the embodiments disclosed herein may be implemented in electronic hardware, or in combination with computer software and electronic hardware. Whether these functions are implemented by hardware or software depends on the particular applications and design constraints of the technical solutions. The skilled people could use different methods to implement the described functions for each of the particular applications, however, such implementations should not be considered as going beyond the scope of the present application.

It should be understood that, in the embodiments of the present application, the disclosed device/terminal device and method could be implemented in other ways. For example, the device described above are merely illustrative; for example, the division of the units is only a logical function division, and other division could be used in the actual implementation, for example, multiple units or components could be combined or integrated into another system, or some features may be ignored, or not performed. In another aspect, the coupling or direct coupling or communicating connection shown or discussed could be an indirect coupling or a communicating connection through some interfaces, devices or units, and the coupling or direct coupling or communicating connection could be electrical, mechanical, or in other form.

An entire or a part of process for implementing the method in the embodiments of the present application can also be accomplished by a computer program product. When the computer program product is executed on the terminal device, the terminal device is caused to implement the steps in the various method embodiments described above.

The aforesaid embodiments are only intended to explain but not to limit the technical solutions of the present application. Although the present application has been explained in detail with reference to the aforesaid embodiments, the person of ordinary skilled in the art that may understand that, the technical solutions disclosed in the embodiments can also be amended, some technical features in the technical solutions can also be equivalently replaced; the amendments or the equivalent replacements don't cause the essence of the corresponding technical solutions to be deviated from the spirit and the scope of the technical solutions in the embodiments of the present application, and thus should all be included in the protection scope of the present application.

What is claimed is:

1. A method for discriminating vertical distribution models of organic carbons in ocean water area, comprising steps of:
    measuring temperatures, salinities and intensities of pressure of a surface layer of an ocean water layer with a Conductivity Temperature Depth (CTD) measurement system;
    calculating depths of water of the ocean water area and depths of mixed layers of the ocean water area using the measured temperatures and salinities of the ocean water area;
    obtaining a concentration of organic carbons in the surface layer of the ocean water area, the depths of water of the ocean water area and the depths of mixed layers of the ocean water area;
    determining different vertical distribution models of organic carbons in the ocean water area according to the concentration of organic carbons in the surface layer of the ocean water area and the depths of water of the ocean water area;
    calculating ratios of the depths of water of the ocean water area to the depths of the mixed layers of the ocean water area;
    discriminating the different vertical distribution models of organic carbons in the ocean water area according to the ratios of the depths of water of the ocean water area to the depths of the mixed layers of the ocean water area;
    determining stocks of organic carbons in water areas corresponding to different vertical distribution models according to the concentration of organic carbons in the surface layer and the vertical distribution models; and
    accumulating the stocks of organic carbons in the water areas corresponding to the different vertical distribution models to obtain the stock of organic carbons in the ocean water area.

2. The method for discriminating vertical distribution models of organic carbons of ocean water area according to claim 1, wherein the step of determining different vertical distribution models of organic carbons in the ocean water area according to the concentration of organic carbons in the surface layer of the ocean water area and the depths of water of the ocean water area comprises steps of:
    classifying the ocean water area into N water areas according to the depths of water of the ocean water area, where N is an integer greater than 1;
    determining N seasonal water features of the N water areas according to a target season; and
    determining the different vertical distribution models according to the N seasonal water features of the N water areas and the concentration of organic carbons in the surface layer of the ocean water area.

3. The method for discriminating vertical distribution models of organic carbons of ocean water area according to claim 2, wherein the step of determining the N seasonal water features of the N water areas according to the target season comprises:
    obtaining water densities of the N water areas according to the target season; and
    determining the N seasonal water features of the N water areas according to the water densities of the N water areas.

4. The method for discriminating vertical distribution models of organic carbons of ocean water area according to claim 2, wherein the step of determining the different vertical distribution models according to the N seasonal water features of the N water areas and the concentration of organic carbons in the surface layer of the ocean water area comprises:
    determining different vertical distribution structures of organic carbons in the N water areas in the target season according to the N seasonal water features of the N water areas;
    determining the different vertical distribution models of organic carbons in the ocean water area according to the different vertical distribution structures of organic carbons in the N water areas in the target season and the concentration of organic carbons in the surface layer of the ocean water area.

5. The method for discriminating vertical distribution models of organic carbons of ocean water area according to claim 1, wherein the step of discriminating the different vertical distribution models according to the ratios of the depths of water of the ocean water area to the depths of the mixed layers of the ocean water area comprises:
    determining discrimination threshold values of the different vertical distribution models of organic carbons in the ocean water area according to the ratios of the depths of water of the ocean water area to the depths of the mixed layers of the ocean water area; and
    discriminating the different vertical distribution models according to the ratios of the depths of water of the ocean water area to the depths of the mixed layers of the ocean water area, and the discrimination threshold values.

6. The method for discriminating vertical distribution models of organic carbons of ocean water area according to claim 5, wherein the step of discriminating the different vertical distribution models according to the ratios of the depths of water of the ocean water area to the depths of the mixed layers of the ocean water area and the discrimination threshold value comprises:
    comparing the ratios of the depths of water of the ocean water area to the depths of the mixed layers of the ocean water area with the discrimination threshold values to obtain comparison results; and
    discriminating the different vertical distribution models of organic carbons in the ocean water area according to the comparison results.

7. The method for discriminating vertical distribution models of organic carbons of ocean water area according to claim 1, wherein after the step of discriminating the different vertical distribution models of organic carbons in the ocean water area according to the ratios of the depths of water of the ocean water area to the depths of the mixed layers of the ocean water area, the method further comprises:
  determining a stock of organic carbons corresponding to each of the different vertical distribution models according to the concentration of organic carbons in the surface layer of the ocean water area and the different vertical distribution models of organic carbons in the ocean water area; and
  accumulating the stock of organic carbons corresponding to each of the different vertical distribution models of organic carbons in the ocean water area, and determining an accumulated value as the stock of organic carbons in the ocean water area.

8. A terminal device, comprising a memory, a processor, and a computer program stored in the memory and executable on the processor, wherein when the computer program is executed by the processor, the processor is configured to:
  measure temperatures, salinities and intensities of pressure of a surface layer of an ocean water layer with a Conductivity Temperature Depth (CTD) measurement system;
  calculate depths of water of the ocean water area and depths of mixed layers of the ocean water area using the measured temperatures and salinities of the ocean water area;
  obtain a concentration of organic carbons in the surface layer of the ocean water area, the depths of water of the ocean water area and the depths of mixed layers of the ocean water area;
  determine different vertical distribution models of organic carbons in the ocean water area according to the concentration of organic carbons in the surface layer of the ocean water area and the depths of water of the ocean water area;
  calculate ratios of the depths of water of the ocean water area to the depths of the mixed layers of the ocean water area;
  discriminate the different vertical distribution models according to the ratios of the depths of water of the ocean water area to the depths of the mixed layers of the ocean water area;
  determining stocks of organic carbons in water areas corresponding to different vertical distribution models according to the concentration of organic carbons in the surface layer and the vertical distribution models; and
  accumulating the stocks of organic carbons in the water areas corresponding to the different vertical distribution models to obtain the stock of organic carbons in the ocean water area.

9. A non-transitory computer readable storage medium which stores a computer program, that, when executed by a processor, causes the processor to implement operations for discriminating vertical distribution models of organic carbons in an ocean water area, comprising:
  measuring temperatures, salinities and intensities of pressure of a surface layer of an ocean water layer with a Conductivity Temperature Depth (CTD) measurement system;
  calculating depths of water of the ocean water area and depths of mixed layers of the ocean water area using the measured temperatures and salinities of the ocean water area;
  obtaining a concentration of organic carbons in the surface layer of the ocean water area, the depths of water of the ocean water area, and the depths of mixed layers of the ocean water area;
  determining different vertical distribution models of organic carbons in the ocean water area according to the concentration of organic carbons in the surface layer of the ocean water area and the depths of water of the ocean water area;
  calculating ratios of the depths of water of the ocean water area to the depths of the mixed layers of the ocean water area;
  discriminating the different vertical distribution models according to the ratios of the depths of water of the ocean water area to the depths of the mixed layers of the ocean water area;
  determining stocks of organic carbons in water areas corresponding to different vertical distribution models according to the concentration of organic carbons in the surface layer and the vertical distribution models; and
  accumulating the stocks of organic carbons in the water areas corresponding to the different vertical distribution models to obtain the stock of organic carbons in the ocean water area.

* * * * *